United States Patent [19]
Matsuoka et al.

[11] 3,966,323
[45] June 29, 1976

[54] APPARATUS FOR PRODUCING TIMING SIGNAL FOR PHOTOMETRIC MEASUREMENT

[75] Inventors: Yoshio Matsuoka; Hiroshi Inomata; Tsuneo Shimazaki; Fujiya Takahata, all of Katsuta, Japan

[73] Assignee: Hitachi, Ltd., Japan

[22] Filed: Nov. 18, 1974

[21] Appl. No.: 524,868

[30] Foreign Application Priority Data
Nov. 21, 1973 Japan............................. 48-130231

[52] U.S. Cl................................. 356/96; 356/240; 250/224; 250/576
[51] Int. Cl.² ........................................... G01J 3/42
[58] Field of Search ............. 356/96, 240; 250/576, 250/224

Primary Examiner—John Kominski
Attorney, Agent, or Firm—Craig & Antonelli

[57] ABSTRACT

Apparatus for producing timing signals for photometric measurement by utilizing light transmitted through samples to be analyzed. The apparatus comprises a light source, a group of sample containing cells, a driving mechanism for moving the sample cells relative to the light source, a concave diffraction grating for dispersing light transmitted through the sample cell, a first photo-detector for receiving a light beam of a predetermined wave length from the concave diffraction grating, a second photo-detector to receive light beams of the zero spectral order subjected to the total refrection at the concave diffraction grating, a signal hold circuit for holding an electric signal available from the first photo-detector, and a command circuitry which responds to the signal held by the hold circuit to produce signals which resets the hold circuit to release the held signal on one hand and on the other hand allows a read-out and/or record apparatus to read out and/or record the peak value of the signal held by the signal hold circuit. A delay circuit may be provided to delay the operation of the command circuit in order that an analog-to-digital conversion of the peak value signal be effected before the read-out thereof.

21 Claims, 10 Drawing Figures

APPARATUS FOR PRODUCING TIMING SIGNAL FOR PHOTOMETRIC MEASUREMENT

BACKGROUND OF THE INVENTION

1. Field of the Invention

The present invention relates in general to a phorometric apparatus and more particularly to an apparatus for producing a signal for timing for operations such as initiation, termination etc. in photometric measurement.

2. Description of the Prior Art

In general, in an automatic sample analysis apparatus or the like e.g. for colorimetrically analyzing successively a series of samples contained in a corresponding number of container cells, the sample container cells are held stationarily, while a light source and a photodetector are moved relative to the stationary cells. Alternatively, the light source and the detector are positioned fixedly, while the sample cells are moved relative to the source lamp and the detector. Such relative movement is effected either continuously or intermittently. In any cases, it is necessary to produce signals for timing the measuring operations in synchronization with the initiation and the termination of the measurement for every sample cell as the cell assembly is displaced.

Hithertofore, it is known that a plate perforated with holes at positions corresponding to those of the sample cells is interposed between a small source lamp and a photo-transistor to thereby produce the timing signals synchronously with the initiation and the termination of the measurement for each cell. According to this known method, the position of the sample cell to be measured is at first detected and subsequently light transmitted through the cell is separately measured. The prior known method is disadvantageous in that the arrangement for producting the timing signals is complicated due to the fact that markings such as impresses have to be formed in the cells and/or switches must be employed for the detection of the cell position in case of a mechanical detecting system, while in the photoelectric detecting system an additional light source and a photo-detector are required for identifying or detecting the position of the sample cell to be measured. Nevertheless, reliability in operation can not be assured or a troublesome calibration or adjustment is required in case an accurate synchronization between the generation of the timing signals and the photometric measurement operations of the sample.

SUMMARY OF THE INVENTION

An object of the present invention is therefore to provide a simplified apparatus which can produce signals for timing the operations in photometric measurement accurately in synchronization with the changing of position of the sample cell under measurement.

According to the invention, there is provided an apparatus for producing timing signals for the operations in photometric measurement, which timing signals are produced by detecting variation at least in a portion of light transmitted through the sample cell as caused by the relative movement between the sample or specimen cells and the light source.

Above and other objects, novel features as well as advantages of the invention will be made more apparent from the following description of preferred embodiments of the invention in conjunction with the annexed drawings.

BRIEF DESCRIPTION OF THE DRAWING

FIG. 6b is a sectional view of the same taken along the line VIb — VIb in FIG. 6a.

DETAILED DESCRIPTION OF THE PREFERRED EMBODIMENTS

Figure 1:
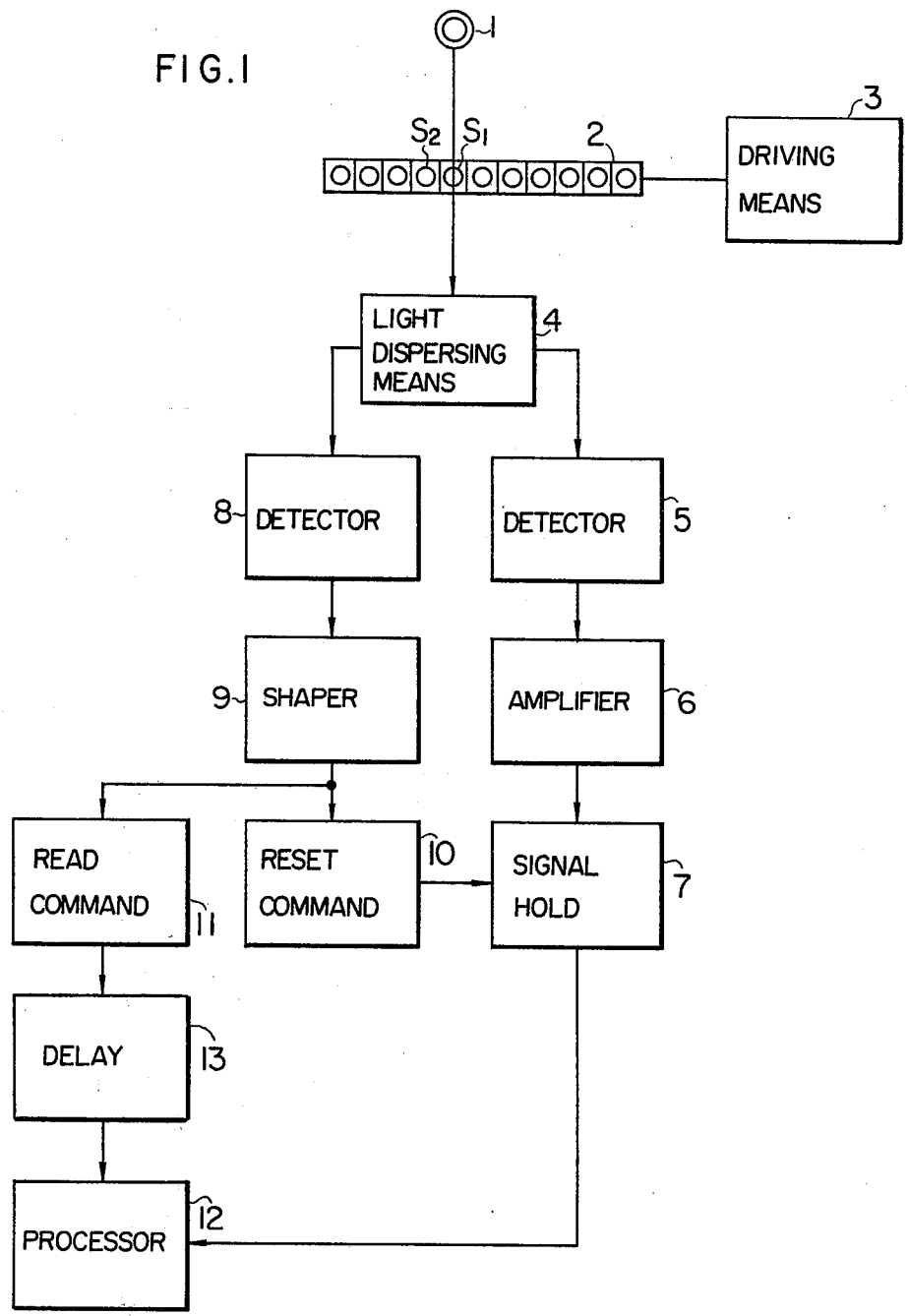
FIG. 1 is a block diagram schematically showing an embodiment of the apparatus according to the invention.
Figure 5:
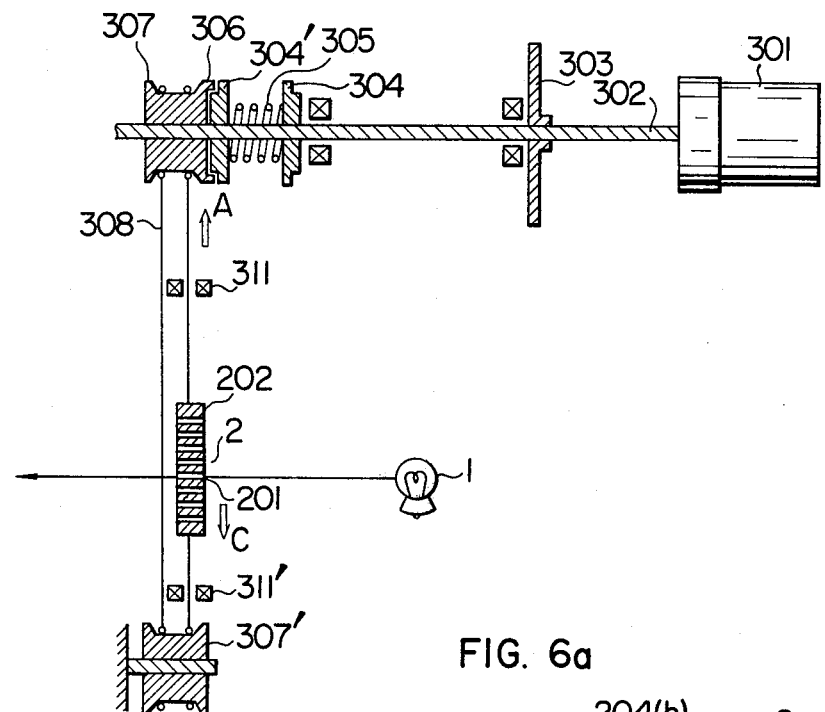
FIG. 5 shows schematically an arrangement of a driving mechanism for moving a sample cell assembly useful in the embodiments of the invention.
Figure 6A:
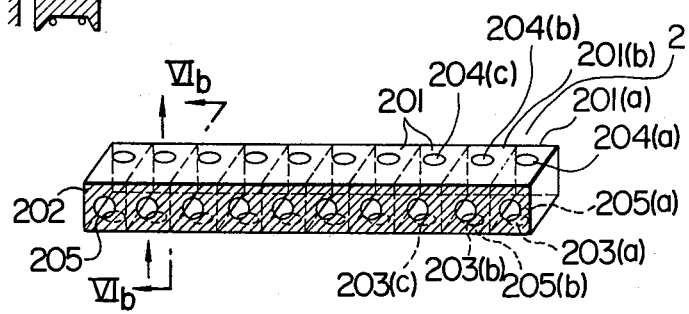
FIG. 6a is a perspective view of a sample container cell assembly for use in the embodiments of the invention.
Figure 6B:
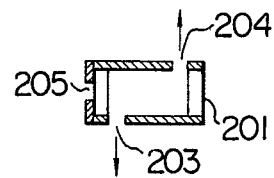

Referring to FIG. 1, reference numeral 1 indicates a light source and 2 denotes an assembly of sample or specimen containers which may be composed of a plurality of absorption cells arranged in a row and disposed in a position to receive a light beam from the light source 1, a detailed arrangement of which is shown in FIGS. 6a and 6b. The sample container or cell assembly 2 is adapted to be moved continuously or intermittently by a driving or feeding mechanism 3, a detailed construction of which will be described hereinafter with reference to FIG. 5. Light emitted by the light source 1 and having transmitted through the one cell of the sample container assembly is applied to a light dispersing means 4 for dispersion of light, a concrete embodiment of which will also be described hereinafter by referring to FIG. 7. Among the dispersed light beams, the light beam of a specific wave length effective for the purpose of photometric measurement of the sample is detected by a first detector means 5 the output of which is coupled to the input of an amplifier means 6, the output from which in turn is connected to the input of a signal holding means 7. An exemplary circuit arrangement of these means is illustrated in detail in FIG. 8. Reference numeral 8 designates a second detector means disposed in a position to sense those of the dispersed light beams other than the light beam effective in photometric measurement of the sample such as those having wave lengths hardly affected in photometric measurement by the sample, or those whose wavelengths include substantially whole range of the wavelengths of the light source, that is those resulted from total reflection by the dispersing means 4, namely the light of the zero order spectrum. Numeral 9 denotes a signal wave shaper circuit which is provided to shape the output signal from the second detector means 8 into a rectangular waveform on the basis of a preset threshold level for detection. Connected to the output of the signal wave shaper circuit 9 is the input of a reset command or signal circuit 10. The output of the reset command circuit 10 is coupled to the input of the signal hold circuit 7 to serve for resetting the holding operation thereof. Further connected to the output of the signal wave shaper circuit 9 is the input of a readout command circuit 11 which has an output coupled to the input of a processor means 12 together with the output from the signal holding circuit 7.

Figure 2:
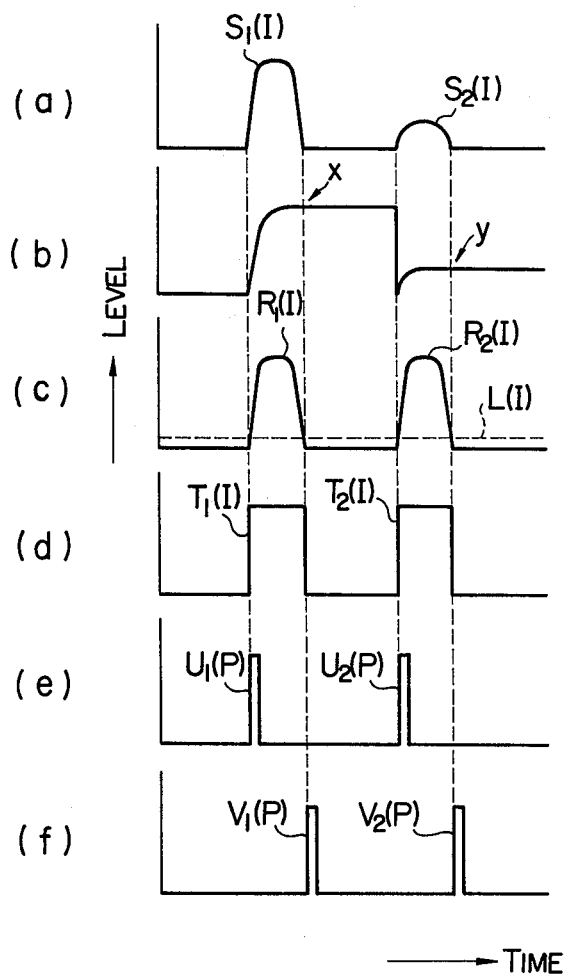
FIG. 2 is a signal wave diagram showing signals for timing the operations in photometric measurement produced in an embodiment of the invention.

In operation of the above described photometric system, the light emitted by the light source 1 transmits through a sample cell such as $S_1$ of the sample container assembly 2 moved continuously or intermittently by the driving mechanism 3 and impinge on the dispersing means 4 thereby to be split into a plurality of light beams having different wave lengths, of which the one having a wavelength effective for the instance purpose constituents thus spectroscopically split and of the photometric measurement or analysis of the sample contained in the container $S_1$ is sensed by the first detector means 5 and subjected to a photo-electric conversion to produce a corresponding electric signal which is applied to the input of the amplifier stage 6 and appears at the output thereof as an amplified sample or specimen signal $S_1(I)$ in a form shown in FIG. 2(a). On the other hand, light split by the dispersing means 4 and undergone the total reflection i.e. light of the zero order spectrum is received by the second detector 8 to be converted into a corresponding electrical signal. Since the light of the zero order spectrum or totally reflected light includes wavelengths extending over substantially the whole region of wavelengths of the light source, the intensity thereof is substantially evaded from the influence exerted by the sample $S_1$ and will remain at a high level as a whole, even if a light of a specific wavelength is absorbed by the sample. The output electric signal produced by the second detector means 8 through the photo-electric conversion can be obtained in a form of a signal wave $R_1(I)$ shown in FIG. 2(c) which is accurately coincident or timelocked with the spectroscopic or sample signal $S_1(I)$ from the amplifier stage 6 shown in FIG. 2(a). When the signal wave $R_1(I)$ is input to the signal wave shaper circuit 9 having a slicing or threshold level such as indicated by L(I) in FIG. 2(c), the signal portion of the wave $R_1(I)$ which is greater than the level L is shaped into a rectangular form by the circuit 9 and appears at the output thereof as a signal wave $T_1(I)$ to be applied to the inputs both of the reset command circuit 10 and the read-out command circuit 11. The reset command circuit 10 is so arranged as to respond the raising or leading edge of the signal wave $T_1(I)$ to thereby produce a reset pulse $U_1(P)$ for resetting the signal holding circuit 7 as shown in FIG. 2(e), while the read-out command circuit 11 utilizes the trailing edge of the signal wave $T_1(I)$ to produce a read-out command signal $V_1(P)$ as shown in FIG. 2(f), which allows the processor 12 to read-out the peak signal value held in the signal holding circuit 7.

If necessary, a delay circuit 13 which may be omitted in each of the embodiments may be preferably interposed between the read-out command circuit 11 and the processor 12 to thereby delay the read-out command pulse signal for a time interval required for the analog to digital conversion of the signal from the signal holding circuit 7 before being transferred to the processor 12.

Upon application of the reset pulse $U_1(P)$ shown in FIG. 2(e), the output from the signal holding circuit 7 is reset to zero state and starts to hold a signal related to the sample signal $S_1(I)$ at a level x corresponding to the peak value of the sample signal $S_1(I)$, which is continued until the next reset pulse $U_2(P)$ produced from the succeeding sample signal $S_2(I)$ is applied to reset againt the signal holding circuit 7, as is indicated in FIG. 2(b). When the read-out command signal pulse $V_1(P)$ appears as shown in FIG. 2(f), the peak value x shown in FIG. 2(b) is then read out by the processor 12, whereby the measurement of the sample contained in the one container or cell $S_1$ has now been completed. In a similar manner, when the next following sample container $S_2$ is subsequently moved to the position to receive the light from the source lamp 1 by means of the driving mechanism 3, light transmitted through the sample container $S_2$ is spectroscopically split and sensed by the first detector means 5 to be converted into a corresponding electric signal which appears as an amplified signal wave $S_2(I)$ shown in FIG. 2(a) at the output of the amplifier 6. On the other hand, light of the zero order spectrum or total reflection light is sensed by the second detector means 8 to be converted into a corresponding electric signal, which is then reformed into a signal wave $T_2(I)$ by the shaper circuit 9 in dependence upon the preset threshold level L(I). Derived from the signal wave $T_2(I)$ are a reset pulse $U_2(P)$ and a read-out command signal $V_2(P)$ which serve, respectively, to reset the signal holding circuit 7 and transfer a peak value signal y held by the signal holding circuit 7 to the processor 12. Similar operations are further repeated to the succeeding sample containers such as $S_3$, $S_4$, etc. which are displaced continuously or intermittently. In this manner, the signals for timing the measuring operations can be obtained which are accurately coincident with the positions of the individual cells of the continuously or intermittently moved sample container assembly 2 on the time basis by utilizing light transmitted through the respective sample containers.

In the above embodiment, light subjected to the total reflection at the light dispersing means 4 or light of the zero order spectrum has been employed to generate the timing signals for the measuring operations. However, it should be appreciated that the invention is never restricted to such arrangement. For example, it is possible to dispose the second detector means 8 at such a position where the detector means 8 can receive instead of the light of the zero order spectrum the light beam of a certain wavelength which is scarcely influenced by the absorption of the specimens in the containers, and which thus can be used to derive therefrom the timing signals for the measuring operations of the photometirc system.

As will be understood from the foregoing description, the aforementioned preferred embodiment of the invention provides an advantage that the timing signals for the measuring operations can be obtained which are accurately synchronized with the increments in the movement of the sample container assembly due to such arrangement that a portion of light which has really transmitted through the sample container is utilized for producing the timing signals. Further, the arrangement is very simple and inexpensive and allows nevertheless photometric analysis of samples with a high reliability.

Figure 3:
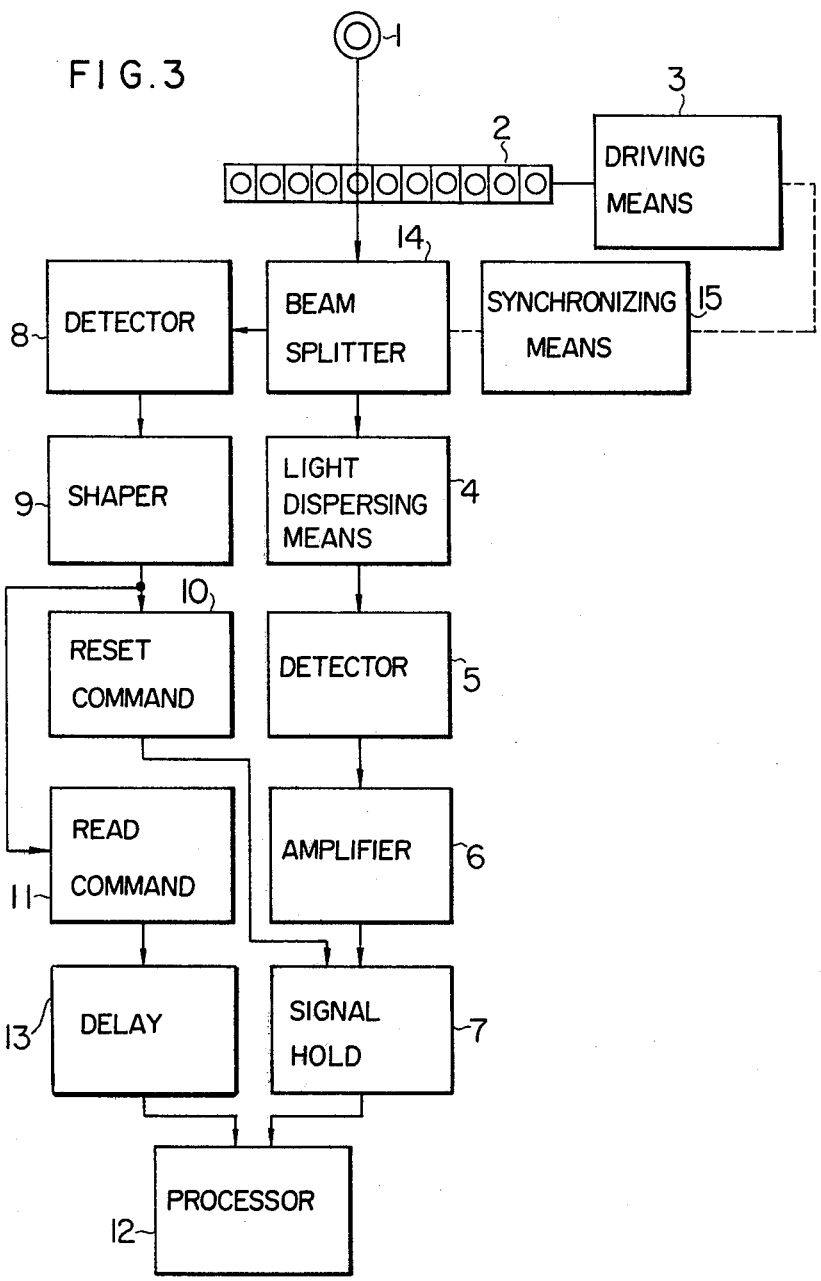
FIG. 3 is a block diagram showing another embodiment of the invention.

FIG. 3 shows in a block diagram another embodiment of a photometric system according to the invention which is differed from the one shown in FIG. 1 in that the light to be transmitted through the sample container is previously divided into two light bundles by means of a beam splitter 14, one of which bundles is then directed to the light dispersing means 4, while the other light bundle is directly applied to the second detector means 8 without passing through the light dispersing means 4. Remaining arrangement of the embodiment shown in FIG. 3 is substantially the same as that of the system described above with reference to FIG. 1. With the arrangement shown in FIG. 3, the timing signals for the measuring operations can be obtained in a similar manner as the timing signals has been derived by utilizing the dispersed light beams undergone the total reflection at the dispersing means 4 in the embodiment shown in FIG. 1.

In this case, it is desirable to provide a synchronizing means 15 to thereby synchronize the movement of the sample cell assembly 2 and the splitting operation of the beam splitter 14.

Figure 4:
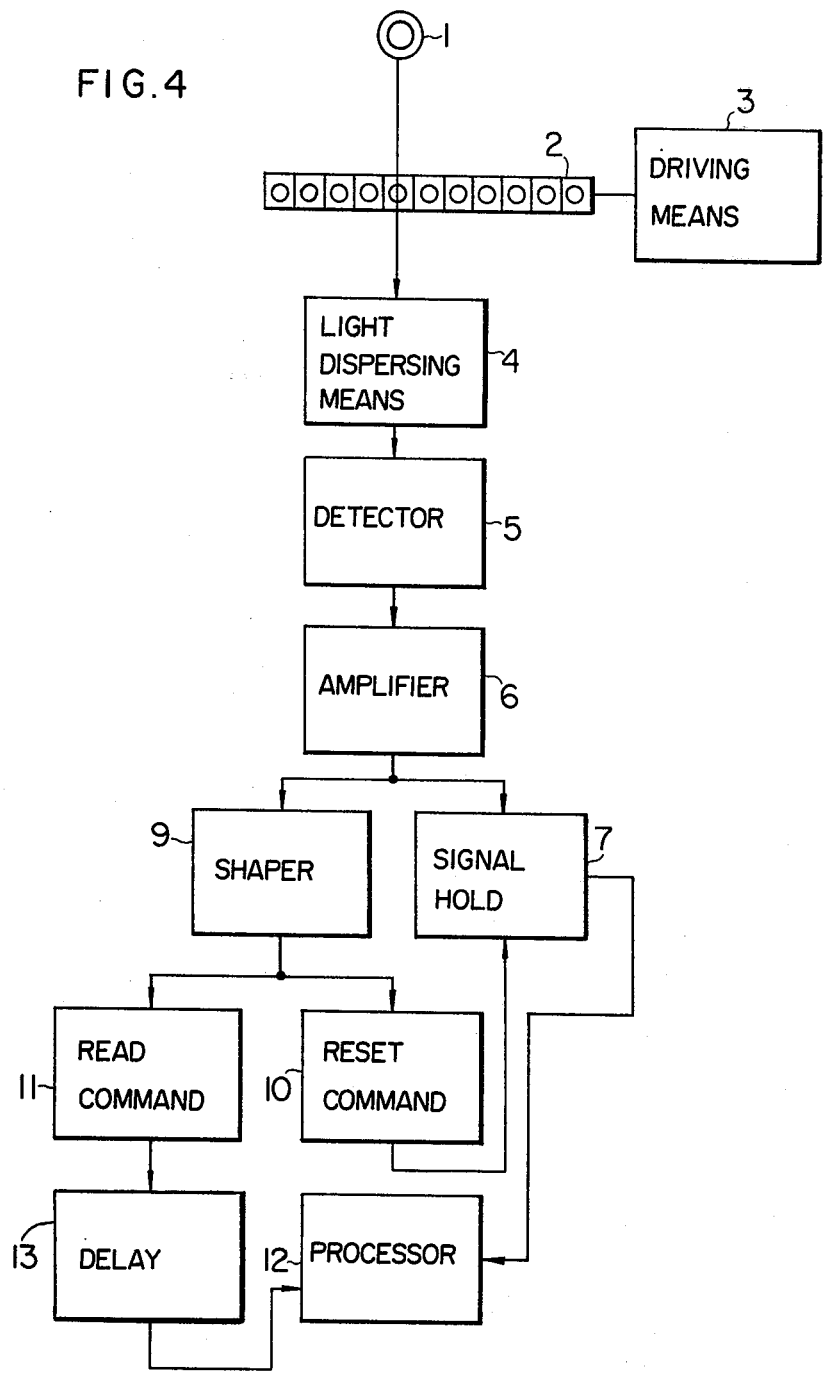
FIG. 4 is a block diagram showing still another embodiment of the invention.
Figure 9:
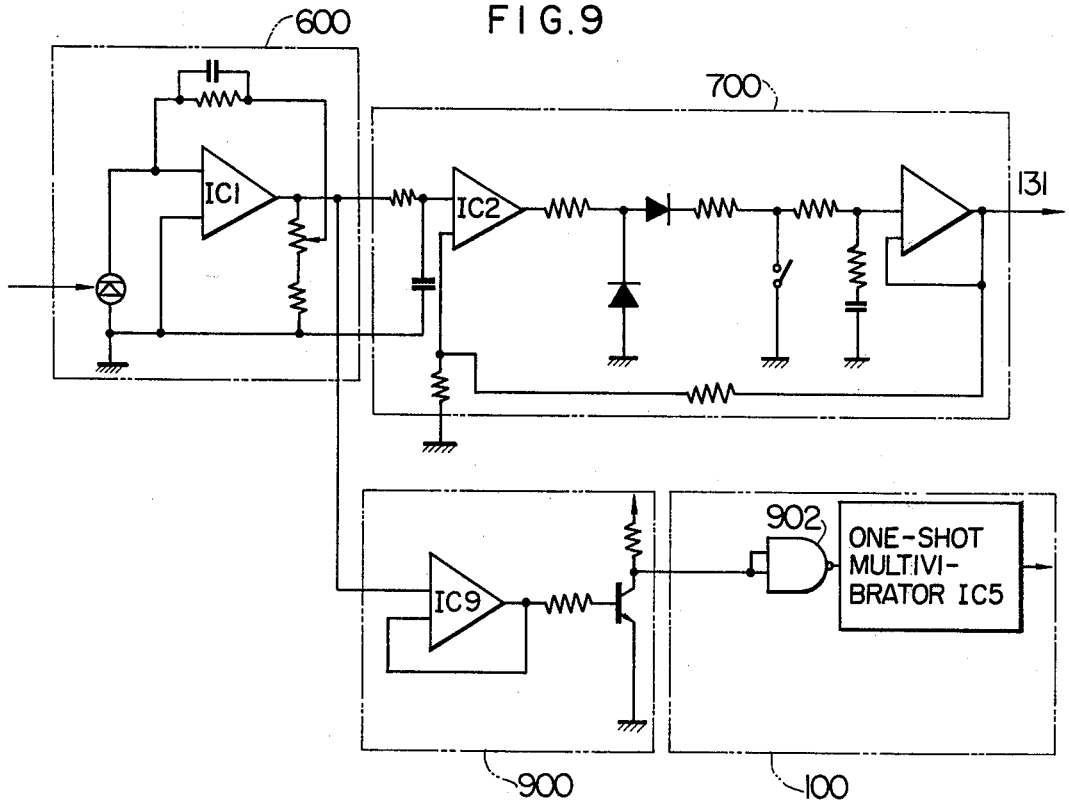
FIG. 9 shows another electric circuit for use in connection with the embodiment shown in FIG. 4.

FIG. 4 shows in a block diagram still another embodiment of the present invention which is differed from the embodiments shown in FIGS. 1 and 3 in respect that the light having the wavelength significant for the measurement of the sample is utilized for the generation of the timing signals for the measuring operations. In case of the embodiment shown in FIG. 4, the second detector means 8 is omitted. Light emitted from the source lamp 1 is applied to a cell of the sample container assembly 2 and the resulted light transmitted through the sample in the cell then impinges on the dispersing means 4, whereupon only the light of the wavelength significant for the analysis of the sample is sensed by the first detector means 5 to be converted into a corresponding electric signal. This signal is subsequently amplified by the amplifier stage 6 and available as a signal in a form shown in FIG. 2(a), which signal is then input to both of the signal holding circuit 7 and the signal wave shaper circuit 9. Exemplary embodiment of these circuits is shown in FIG. 9. Further operations of the system shown in FIG. 4 are substantially the same as those of the embodiments shown in FIGS. 1 and 3.

In the embodiments shown in FIGS. 3 and 4, the dispersing means 4 may be omitted if the light source is arranged to produce a monochromatic light.

Referring to FIG. 5 which schematically shows an exemplary construction of the driving mechanism 3 for the sample container assembly 2, reference numeral 301 indicates an electric motor to rotate a shaft 302 on which a gear wheel 303 is mounted and used optionally for feeding intermittently the sample container assembly 2. A pair of spring seats 304 and 304' are fixedly mounted on the shaft 302 for receiving a compression spring 305 therebetween. The spring seat 304' is operatively connected to a cord winding pulley 307 through a frictional coupling portion 306. The pulley 307 is thus rotatable under the influence of the spring 305 to which a rotational torque is applied from the motor 301 through the shaft 302. The cord or string 308 is spanned over the pulleys 307 and 307' in a tensioned state. Free ends of the tensioned cord 308 are secured to the sample container assembly 2 which is disposed between the pulleys 307 and 307' and comprises a plurality of sample cells 201 and a base portion 202 as will be described in more detail hereinafter. The base portion 202 is supported on a supporting structure not shown for a reciprocated movement. It will be understood that rotations of pulley 307 will move the sample cells 201 and the base portion 202 in a unit forwardly or backwardly.

In operation, the rotation of the electric motor 301 in one direction will rotate the pulley 307 through the shaft 302 in such a direction that the cord 308 may draw constantly the sample cell assembly 2 in the forward direction indicated by an arrow A. When the sample cell assembly 2 bears against a stopper 311, the rotation of the electric motor 301 is reversed in response to a signal produced by a suitable means not shown. The pulley 307 is thus rotated in the other direction to draw the sample cell assembly 2 through the cord 308 in the backward direction indicated by an arrow C. When the sample cell assembly 2 reaches another stopper 311', the former stops at a position where the sample cells 201 may be filled with liquid samples to be analyzed through associated suction nozzles not shown. After the cells have been filled with a predetermined amount of liquid samples, the electric motor 301 is rotated to move the sample cell assembly 2 in the forward direction, during which the individual sample cells 201 are successively projected by a light beam from the light source lamp 1 and resulted transmission of light are evaluated and recorded for the analytical measurements in the process as hereinbefore described.

Referring to FIG. 6a which shows an exemplary construction of the sample cell assembly in a perspective view, the sample cell assembly indicated by the numeral 2 comprises individual sample cells or containers 201(a), 201(b), etc. of a colorless transparent material having a good transmission factor provided in number corresponding to that of items for measurement. The individual cells are formed with inlet ports 203(a), 203(b), etc. and exit ports 204(a), 204(b), etc. in the top and bottom portions thereof, respectively, to allow the flow of liquid samples into and out of the respective cells. Numerals 205(a), 205(b), etc. indicate light transmitting surfaces of the associated sample cells 201(a), 201(b), etc. The sample containers are shielded at the sides which receive the light from a base member or mask 202 having holes disposed with an equal distance therebetween at positions corresponding to the respective light transmitting surfaces. Among these sample containing cells, the cell 201(a) which is first projected by the light may be employed for setting the transmission factor of zero, while the next sample cell 201(b) may be used to set the transmission factor of 100%, for example. The remaining cells 201(c), 201(d), etc. may be then used for measuring the absorption spectra of the samples.

FIG. 6b shows the sample container cell assembly in a sectional view taken along the line VIb — VIb in FIG. 6a.

Figure 7:
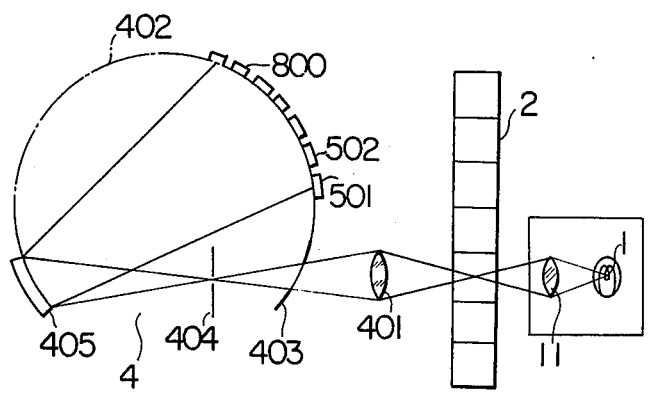
FIG. 7 shows an exemplary embodiment of a light dispersing means useful in some embodiments of the invention.

Referring to FIG. 7 which shows schematically a typical construction of the light dispersing means which can be advantageously used in the system embodying the present invention, light from the source lamp 1 is focused at a point on the sample container cell assembly 2 through a condenser lens 11. The dispersing means 4 comprises a lens 401 for forcusing light transmitted through the sample, an entrance slit 403 positioned on a Rowland circle 402, an intermediate slit 404, a concave diffraction grating 405 having its center disposed on the Rowland circle 402, a plurality of detectors 501, 502, etc. disposed also on the Rowland circle 402 and a detector 800 for sensing the light of the zero order spectrum. It is to be noted that the light source 1, lines 11, sample cell assembly 2, lens 401 and entrance slit 403 are disposed equidistantly from one another.

A plurality of light beams of different wavelengths produced by the concave diffraction grating 405 are sensed by the plurality of detectors 501, 502, etc. placed on the Rowland circle 402 and converted into corresponding electric signals which are thereafter fed to the associated processing circuitries as aforementioned. The other detector 800 placed on the Rowland circle is destined to receive the light of the zero order spectrum or the portion of light subjected to the total reflection at the concave diffraction grating 405 and produce a corresponding electric signal which is applied to the signal wave shaper circuit 900.

Figure 8:
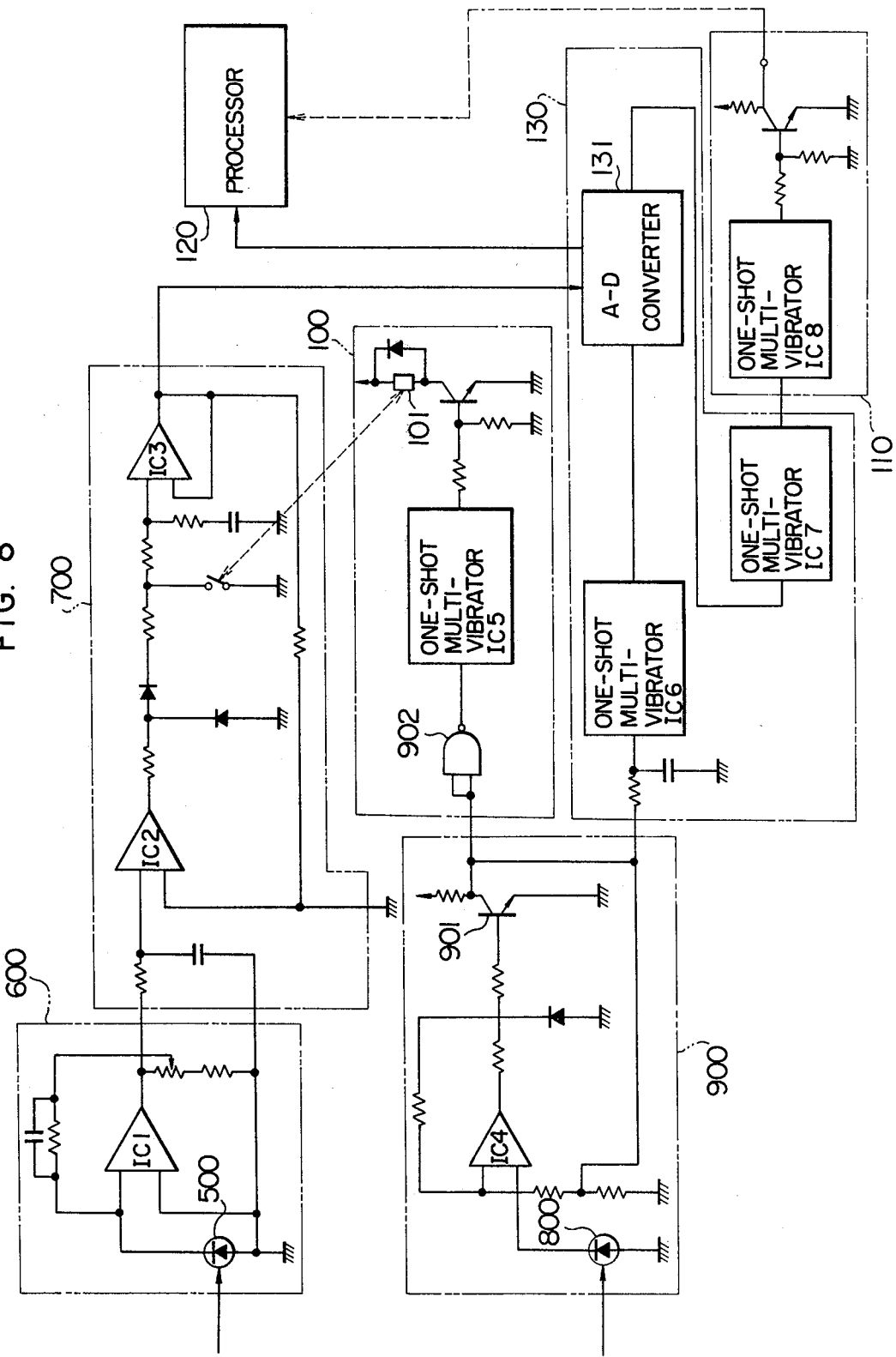
FIG. 8 is a circuit diagram showing an exemplary electric circuit for use in some embodiments of the invention.

FIG. 8 shows an electric circuit arrangement which may be employed in the aforementioned embodiments of the inventive system. In the drawing, a monochromatic light beam split by the concave diffraction grating 405 is received by a detector 500 and converted into a corresponding electric signal. Since the signal current is relatively low, it is amplified by an amplifier 600 and thereafter supplied to a signal holding circuit 700. At the same time, the light of the zero order spectrum or the portion of light having wavelength scarcely influenced by the sample is sensed by the second photodetector 800 and after the photo-electric conversion the corresponding electric signal is introduced to the signal wave shaper circuit 900, to thereby saturate an operational amplifier IC4 of the shaper circuit 900 in the positive or negative direction. Since the saturation of the amplifier IC4 from 0 to 1 level upon the impingiment of light onto the photodetector 800 will simultaneously cause the switching of the transistor 901 from 1 to 0 level and hence the output of NAND gate 902 from 0 to 1 level, a mono-stable or one-shot multivibrator IC5 will produce a pulse upon the impingement of light. This pulse will turn on a relay 101 of a reset command circuit 100 and reset the signal holding circuit 700 to the state ready for holding a signal. The signal holding circuit 700 serves to hold the peak value of the output signal from the amplifier circuit 600 and fed the held value to an analog-to-digital coverter 131 integrated in a delay circuit 130. When light is again interrupted, the circuit IC4 is switched from 1 to 0, whereupon a one-shot multivibrator IC6 is triggered. While the circuit IC6 produces a pulse, the analog-to-digital converter 131 receives the input. In other words, the peak value signal held by the holding circuit 700 is taken out and subjected to the analog-to-digital conversion. Upon completed analog-to-digital conversion, the converter 131 produces a corresponding pulse which makes one-shot multivibrators IC7 and IC8 of a read-out command circuit 110 to be operative, whereby a processor 120 can print out the digital signal representative of the monochromatic light beam significant for the sample. In this way, the delay circuit 130 is provided in order to assure the time interval required for the analog-to-digital conversion and to hold a stabilized value at the time of printing out the measurement signal.

It will be appreciated that the rate of feeding the sample cell assembly can be determined in consideration of the time for the analog-to-digital conversion and the time for printing out the measured results.

FIG. 9 shows an electric circuit which can be employed in combination with the embodiment shown in FIG. 4. This circuit is differed from the one shown in FIG. 8 in that the output from the amplifier circuit is divided into two portions, one of which is applied to the signal holding circuit, while the other is fed to the signal wave shaper circuit. The remaining circuit arrangement of FIG. 9 is substantially similar to that of FIG. 8. It is seen that the circuit shown in FIG. 9 can perform substantially the same operation as that of the circuit shown in FIG. 8 with a much simplified construction as compared with the latter.

We claim:

1. An apparatus for producing signals for timing the operations in photometric measurement comprising a light source, a plurality of containers for samples, driving means for providing a relative movement between said light source and said plurality of sample containers, means for detecting variation at least in a portion of light transmitted through said sample container and for providing a detection signal in accordance therewith, said variation being caused by said relative movement, and means for deriving signals for timing the operations of measuring said samples contained in said container from the detection signal produced by said detecting means, whereby said timing signals are produced on the basis of light transmitted through said containers.

2. An apparatus as set forth in claim 1, further comprising processing means responsive to said detecting means for processing the detection signals in accordance with the timing signals.

3. An apparatus according to claim 2, wherein said processing means includes means for at least one of reading out and recording.

4. An apparatus for producing signals for timing the operations in photometric measurement, comprising a light source, a plurality of containers for samples, driving means for moving said plurality of sample containers relative to said light source, dispersing means for dispersing light transmitted through said sample containers, first detecting means for receiving a first portion of light from said spectroscopic means, second detecting means for receiving a second portion of light from said spectroscopic means, means for holding an electric signal derived from said first detecting means, and means to utilize an electric signal derived from said second detector means for producing a command signal to release the holding of said electric signal held in said holding means and a command fed to a processing means to one of read-out and record a value of said signal held by said holding means at the peak level thereof, whereby said timing signals are produced on the basis of light transmitted through said containers.

5. An apparatus as set forth in claim 4, further comprising delay means for delaying said command signal from said command means to said processing means for a time duration required for an analog-to-digital conversion of said signal value held by said holding means at a peak level.

6. An apparatus as set forth in claim 4, wherein said dispersing means comprises a concave diffraction grating and said first portion of light of the zero order spectrum undergone the total reflection at said concave diffraction grating.

7. An apparatus as set forth in claim 4, wherein said dispersing means comprises a concave diffraction grating and said first and second detecting means are disposed on the Rowland circle having a diameter corresponding to the radius of curvature of said concave diffraction grating, said first detecting means being adapted to receive a portion of light having a wavelength significant for the measurement of said sample among light beams dispersed by said concave diffraction grating, and said second detecting means being adapted to receive a portion of light having a predetermined wavelength scarcely susceptible to influence of said samples.

8. An apparatus as set forth in claim 4, wherein said signal holding means is composed of an amplifier circuit for amplifying electric signal from said first detecting means and a signal hold circuit to hold a maximum output signal from said amplifier circuit, while said command means is composed of a signal wave shaper circuit for shaping electric signal from said second detecting means at a level greater than a preset threshold value, a reset command circuit for feeding a hold resetting command to said hold circuit in response to the leading edge of said shaped signal output from said signal wave shaper circuit, and a circuit for producing a command signal in response to the trailing edge of said shaped signal, which command signal allows said processing means to one of read out or record a peak value of said signal held by said hold circuit.

9. An apparatus for producing signals for timing the operations in photometric measurement comprising a light source, a plurality of sample containers, driving means for moving said plurality of sample containers relative to said light source, beam splitter means for splitting light transmitted through said sample container into two light bundles, dispersing means for dispersing a first light bundle from said beam splitter means, first detecting means to receive a portion of light having a wavelength significant for the measurement of said sample among dispersed light rays from said dispersing means, second detecting means to receive a second light bundle from said beam splitter means, means for holding an electric signal available from said first detecting means, a command means for responding to an electric signal from said second detecting means to produce a command for releasing or resetting said signal held by said signal holding means and a command to allow signal processing means to one of read out and record a peak value of said signal representative of measured event held by said holding means, whereby said timing signals are produced on the basis of light transmitted through said containers.

10. An apparatus as set forth in claim 9, further comprising delay means for delaying said command signal from said command means to said processing means for a time duration required for an analog-to-digital conversion of said signal value held by said holding means at a peak level.

11. An apparatus as set forth in claim 9, wherein said signal holding means is composed of an amplifier circuit for amplifying electric signal from said first detecting means and a signal hold circuit to hold a maximum output signal from said amplifier circuit, while said command means is composed of a signal wave shaper circuit for shaping electric signal from said second detecting means at a level greater than a preset threshold level, a reset command circuit for feeding a hold resetting or releasing command to said hold circuit in response to the leading edge of said shaped signal output from said signal wave shaper circuit, and a circuit for producing a command signal in response to the trailing edge of said shaped signal, which command signal allows said processing means to one of read out and record a peak value of said signal held by said hold circuit.

12. An apparatus for producing signals for timing the operations in photometric measurement, comprising a light source, a plurality of sample containers, driving means for moving said plurality of sample containers relative to said light source, dispersing means for splitting the light transmitted through said containers, detecting means to receive only a portion of light having a wavelength significant for the measurement of said sample from said dispersing means, holding means to hold electric signal output from said detecting means, and command means for responding to said output electric signal from said detecting means to produce a command signal for releasing said signal held by said holding means and a command signal which allows a processing means to one of read out and record a peak value of said signal held by said holding means representative of measured event, whereby said timing signals are produced on the basis of light transmitted through said sample container.

13. An apparatus as set forth in claim 12, further comprising delay means for delaying said command signal from said command means to said processing means for a time duration required for an analog-to-digital conversion of said signal value held by said holding means at a peak level.

14. An apparatus as set forth in claim 12, wherein said detecting means comprises a photo-detector circuit to receive from said dispersing means only a portion of light having a wavelength significant for the measurement of said sample and convert said portion of light into a corresponding electric signal and an amplifier circuit for amplifying said electric signal from said photo-detector circuit, while said holding means comprises a hold circuit to hold a maximum output electric signal from said amplifier circuit, and on the other hand said command means comprises a signal wave shaper circuit for shaping the electric signal significant for said sample as output from said amplifier circuit at a level greater than a preset threshold value, a reset command circuit for responding to the leading edge of said shaped signal from said signal wave shaper circuit to supply a reset command to said hold circuit and a circuit which responds to the trailing edge of said shaped signal to supply a command to a processing means to thereby one of read out and record a peak value of the signal held by said hold circuit.

15. An apparatus for producing signals for timing the operations in photometric measurement, comprising a light source adapted to emit light of a predetermined wavelength, a plurality of sample containers disposed at a position to be projected by light from said light source, driving means for moving said plurality of sample containers relative to said light source, means for dividing monochromatic light transmitted through said sample container during said relative movement between said sample containers and said light source to a first and a second detecting means, means for holding an electric signal available from said first detecting means, and command means for responding to an electric signal available from said second detecting means to produce a command signal to release said signal held by said holding means and a command signal which allows a processing means to one of read-out and record a peak value of said signal held by said holding means representative of a measured event, whereby said timing signals are produced on the basis of light transmitted through said sample containers.

16. An apparatus as set forth in claim 15, further comprising delay means for delaying said command signal from said command means to said processing means for a time duration required for an analog-to-digital conversion of said signal value held by said holding means at a peak level.

17. An apparatus for producing signals for timing the operations in photometric measurement comprising a light source adapted to emit light of a predetermined wavelength, a plurality of sample containers disposed at a position to be projected by light from said light source, driving means for moving said plurality of sample containers relative to said light source, detecting means to receive monochromatic light transmitted through said sample container during said relative movement between said sample containers and said light source, holding means to hold an electric signal available from said detector means, command means for responding to said electric signal available from said detecting means to produce a command signal for releasing said signal held by said holding means and a command signal which allows a processing means to one of read out and record a value of said signal held by said holding means at a peak level, whereby said timing signals are produced on the basis of light transmitted through said samples.

18. An apparatus at set forth in claim 17, further comprising delay means for delaying said command signal from said command means to said processing means for a time duration required for an analog-to-digital conversion of said signal value held by said holding means at a peak level.

19. An apparatus for producing signals for timing the operations in photometric measurement, wherein said timing signal is derived from light transmitted through samples to be measured comprising a light source, a plurality of sample containers arranged so as to be projected successively by light from said light source, a driving mechanism for moving said sample containers relative to said light source, a concave diffraction grating for spectroscopically splitting light transmitted through said sample containers, a first photo-detector to receive a light beam having a predetermined wavelength among light beams dispersed by said concave diffraction grating, a second photo-detector to receive light beams of the zero order spectrum subjected to the total reflection at said concave diffraction grating, an amplifier circuit for amplifying an electric signal from said first photo-detector corresponding to said light beam having a predetermined wavelength, a hold circuit to hold the amplified signal from said amplifier circuit at a peak value thereof, a signal wave shaper circuit for shaping an electric signal from said second photo-detector corresponding to said light beam of the zero order spectrum at a level greater than a preset threshold value, a reset command circuit for responding to the leading edge of the shaped electric signal from said signal wave shaper circuit to supply a reset signal to said hold circuit, a read-out command circuit for responding to the trailing edge of said shaped signal to produce a command signal which allows a processing apparatus apparatus to at least one of read-out and record the peak value of the signal held by said hold circuit, and a delay circuit for delaying the command operation of said read-out command circuit for a time duration required for an analog-to-digital conversion of said peak value signal.

20. An apparatus for producing a signal for timing the operations in photomeric measurement, wherein said timing signal is derived from light transmitted through samples to be measured, comprising a light source, a plurality of sample containers arranged so as to be successively illuminated with light from said light source, a driving mechanism for moving said sample containers relative to said light source, a beam splitter for dividing light transmitted through said sample container into first light bundle and a second light bundle, dispersing means for splitting said first light bundle from said beam splitter, a first photo-detector to receive a light beam of a predetermined wavelength from said dispersing means, a second photo-detector to receive said second light bundle, an amplifier circuit to amplify an electric signal from said first photo-detector corresponding to said light beam of the predetermined wavelength, a hold circuit for holding the amplified signal from said amplifier circuit at a peak value thereof, a signal wave shaper circuit for shaping electric signal from said second photo-detector at a level greater than a preset threshold value, a reset command circuit for responding to the leading edge of the shaped signal from said signal wave shaper circuit to produce a reset command to said hold circuit, a read-out command circuit for responding to the trailing edge of the shaped signal from said shaper circuit to produce a command signal which allows a processing apparatus to at least one of read-out and record the peak value of the signal held by said hold circuit, and a delay circuit for delaying the command operation of said read-out command circuit for a time duration required for an analog-to-digital conversion of said peak value signal.

21. An apparatus for producing a signal for timing the operations in photometric measurement, wherein said timing signal is derived from light transmitted through samples to be measured, comprising a light source, a plurality of sample containers arranged so as to be successively projected by light from said light source, a driving mechanism to move said sample containers relative to said light source, dispersing means for splitting light transmitted through said sample container, a photo-detector to receive a light beam of a predetermined wavelength significant for said sample from said dispersing means, an amplifier circuit for amplifying electric signal from said photo-detector, a hold circuit for holding the amplified signal from said amplifier circuit at a peak value thereof, a signal wave shaper circuit for shaping said amplified electric signal from said amplifier circuit at a level greater than a preset threshold value, a reset command circuit for responding to the leading edge of the shaped signal from said signal wave shaper circuit to supply a reset command to said hold circuit, a read-out command circuit for responding to the trailing edge of said shaped signal to produce a command which allows a processing apparatus to at least one of read-out and record the peak value signal held by said hold circuit, and a delay circuit for delaying the command operation of said read-out command circuit for a time duration required for an analog-to-digital conversion of said peak value signal.

* * * * *